US009504707B2

(12) United States Patent
Nowakowska et al.

(10) Patent No.: US 9,504,707 B2
(45) Date of Patent: Nov. 29, 2016

(54) USE OF THE MODIFIED POLYSACCHARIDES FOR HEPARIN NEUTRALIZATION

(75) Inventors: Maria Nowakowska, Cracow (PL); Krzysztof Szczubiałka, Krzywaczka (PL); Kamil Kamiński, Zawoja (PL)

(73) Assignee: UNIWERSYTET JAGIELLONSKI, Crakow (PL)

( * ) Notice: Subject to any disclaimer, the term of this patent is extended or adjusted under 35 U.S.C. 154(b) by 20 days.

(21) Appl. No.: 13/642,279

(22) PCT Filed: Apr. 20, 2011

(86) PCT No.: PCT/PL2011/000040
§ 371 (c)(1),
(2), (4) Date: Oct. 19, 2012

(87) PCT Pub. No.: WO2011/133052
PCT Pub. Date: Oct. 27, 2011

(65) Prior Publication Data
US 2013/0034516 A1    Feb. 7, 2013

(30) Foreign Application Priority Data
Apr. 22, 2010  (PL) ........................................ 391043

(51) Int. Cl.
*A61K 31/717* (2006.01)
*A61K 31/721* (2006.01)

(52) U.S. Cl.
CPC ........... *A61K 31/717* (2013.01); *A61K 31/721* (2013.01)

(58) Field of Classification Search
None
See application file for complete search history.

(56) References Cited

U.S. PATENT DOCUMENTS 4,131,576 A * 12/1978 Iovine .................. C08F 251/00
                                                          527/312
4,411,891 A * 10/1983 Mizutani et al. ............... 514/59
5,416,198 A * 5/1995 Anderson et al. ............ 536/111
2002/0146826 A1* 10/2002 Domb .......................... 435/455
2003/0040125 A1* 2/2003 Bernatchez et al. .......... 436/518

FOREIGN PATENT DOCUMENTS

WO          9310899 A2    6/1993
WO       2010093269 A1    8/2010

OTHER PUBLICATIONS

Szczubialka et al. "Smart anionic polyelectrolytes based on natural polymer for complexation of cationic surfactant," Journal of Applied Polymer Science 102:2401-2407, 2006.*
Merriam Webster definition of "Administration" printed 2014.*
Montalescot et al. "Neutralization of low molecular weight heparin by Polybrene prevents thromboxane release and severe pulmonary hypertension in awake sheep," Circulation 82(5):1754-1764, 1990.*
Abe et al. "Polybrene increases the efficiency of gene transfer by lipofection," Gene Therapy 5:708-711, 1998.*
Sahiner et al. "Microgel, nanogel and hydrogel-hydrogel semi-IPN composites for biomedical applications: synthesis and characterization," Colloid and Polymer Science 284:1121-1129, 2006.*
Ferraris et al. "Perioperative blood transfusion and blood conservation in cardiac surgery: the society of thoracic surgeons and the society of cardiovascular anesthesiologists clinical practice guidelines," The Annals of Thoracic Surgery 83:S27-86, 2007.*
Bromfield et al. "Heparin sensing and binding—taking supramolecular chemistry towards clinical applications," Chemical Society Reviews 42(23):9184-9195, 2013.*
Thomas, et al.; "Dextran—glycidyltrimethylammonium chloride conjugate/DNA nanoplex: A potential non-viral and haemocompatible gene delivery system"; International Journal of Pharmaceutics; Apr. 15, 2010; pp. 195-206; vol. 389; Nr: 1-2; Elsevier BV; NL.

* cited by examiner

*Primary Examiner* — David J Blanchard
*Assistant Examiner* — Alissa Prosser
(74) *Attorney, Agent, or Firm* — Walker & Jocke

(57) ABSTRACT

The subject of the invention is the use of cationically modified polysaccharides, except for chitosan, for direct neutralization of heparin in blood and physiological fluids in a mammal. Cationic modification of the polysaccharides is achieved using compound containing cationic ammonium groups and/or the polysaccharides are grafted with a polymer containing amine and/or ammonium groups.

4 Claims, 5 Drawing Sheets a)

b)

USE OF THE MODIFIED POLYSACCHARIDES FOR HEPARIN NEUTRALIZATION

The subject of the invention is the use of the modified polysaccharides for heparin neutralization directly in blood and other physiological fluids.

Heparin, a substance discovered by McLean almost a century ago, has found clinical applications since 1937 and is a first polysaccharide-based drug, which is widely applied in the therapy of humans. Heparin is a complex mixture of glucosaminoglycans (GAG) of high degree of sulfation (with 2.7 negative charges in a disaccharide repeating unit it has the highest density of the negative charge among biological molecules) which is produced and stored in the mast cells of animals (e.g. in bovine intestines or porcine lungs). It very strongly inhibits blood clotting, although only one third of heparin molecules shows anticoagulant properties. Its action is based on enhancing the ability of antithrombin (AT) to deactivate thrombin and Xa factor, which are enzymes responsible for blood clotting. Therefore, heparin is a drug of choice in situations, when obtaining fast anticoagulant effect is necessary, e.g. during surgical procedures, particularly to prevent formation of blood clots in the apparatus used in the extracorporeal therapy such as dialysers and oxygenators. It also has many other therapeutical applications, e.g. in the treatment of unstable angina pectoris or acute myocardial infarct.

However, administration of heparin involves many adverse effects, among which the most frequent are bleeding, heparin induced thrombocytopenia (HIT), and osteoporosis.

Therefore, it is often necessary to neutralize or remove heparin from the bloodstream after its desired anticoagulant effect is obtained. A series of methods of its removal has been developed. Usually this is achieved by the administration of protamine, a protein introduced to the clinical practice as a heparin antagonist almost simultaneously with heparin (Fischer, A Biochem Zeit. 278, 133, 1935). It shows high content of basic aminoacids (such as arginine, lysine, and histidine) which may reach 80%. Another polymer used to remove heparin is poly-L-lysine (Ma, X., Mohammad, S. F., Kim, S. W. Biotechnology and Bioengineering Volume 40, Issue 4, 5 Aug. 1992, Pages 530-536), which is used also to enhance action of protamine sulfate. Yet another approach to the problem of heparin removal is its enzymatic degradation using immobilized heparinase (Kolde, H.-J., Pelzer, H., Borzhenskaya, L., Russo, A., Rose, M., Tejidor, L. Hamostaseologie Volume 14, Issue 1, 1994, Pages 37-43).

Unfortunately, the above mentioned methods of heparin removal may themselves induce side effects. Protamine sulfate, if left non-neutralized or removed from the bloodstream, may result in adverse reactions in about 10% of patients. They may be very severe, even fatal, and include pulmonary hypertension, arterial hypotension, anaphylactic shock, thrombocytopenia, granulocytopenia, complement activation and cytokine release. Neutralization of heparin with protamine sulfate is not complete and is accompanied with allergic reactions. On the other hand, poly-L-lysine is still quite an expensive polymer.

Many attempts to construct devices for heparin removal have been undertaken, mostly based on the application of immobilized poly-L-lysine (Joseph B. Zwischenberger, MD, Roger A. Vertrees, BA, CCP, Robert L. Brunston, Jr., MD, Weike Tao, MD, Scott K. Alpard, MD, and Paul S. Brown, Jr., MD, The Journal of Thoracic and Cardiovascular Surgery 1998 Volume 115, Number 3; Zwischenberger, J. B., Tao, W., Deyo, D. J., Vertrees, R. A., Alpard, S. K., Shulman, G. Annals of Thoracic Burgery Volume 71, Issue 1, 2001, Pages 270-277). The heparin removal device (HRD) described in the above papers was extracorporeally included in the patient's bloodstream by veno-venous circuit. It separates plasma, which upon heparin removal by contact with poly-L-lysine, is returned to the patient's blood. Despite the promising experimental data, there has been only limited experience with such heparin removal devices, and none of them have been clinically implemented until now. A method frequently used to avoid complications brought about by free heparin antagonists is their immobilization on polymeric supports inside the heparin removal devices. For example, protamine was supported on a matrix obtained by grafting an acrylic polymer onto cellulose (Hou, K. C., Roy, S., Zaniewski, R., Shumway, E. Artificial Organs Volume 14, Issue 6, 1990, Pages 436-442) or inside cellulose fibres (Wang, T., Byun, Y., Kim, J.-S., Liang, J., Yang, V. C. International Journal of Bio-Chromatography Volume 6, Issue 2, 2001, Pages 133-149). It was shown that the bioreactor removed more than 50% of administered heparin during 10 minutes at the blood flow rate of 100 ml/min. While fast injection of protamine in dogs results in acute hypotension, application of a bioreactor containing immobilized protamine did not result in any statistically significant changes in monitored hemodynamic parameters. Another paper reports efficient removal of heparin using beads obtained from alginate and poly-L-lysine (M. Sunil Varghese, D. Hildebrandt, and D. Glasser, N. J. Crowther, D. M. Rubin, Artificial Cells, Blood Substitutes, and Biotechnology, 34: 419-432, 2006).

It is a well-known fact that polysaccharides are used for many medical applications. For example dextran a glucose-based polymer with high molecular mass, is used as a blood substitute. Chitin, a polysaccharide of animal origin, is used for enzyme immobilizing thanks to its biodegradability, lack of toxicity, physiological inertness, antibacterial properties, ability to form gels and an affinity to peptides. Chitin could be also applied for wound treatment. Chitosan obtained from chitin can be also used for this purpose. Hyaluronic acid is another example of a polysaccharide that has many applications in medicine including viscosupplementation of joints, smoothing of wrinkles and moisturizing of skin. This polysaccharide is often used in ophthalmology for example in the surgical treatment of cataract, to speed up healing of cornea and increasing stability of atropine preparations. Gels made using alginate, a polysaccharide obtained from sea algae is applied for encapsulation of enzymes and cell culturing. Many other polysaccharides, e.g. pectins, glucomannans, galactomannans, xanthans also have medical applications. Recently it was found that a chitosan polymer cross-linked with genipin can remove heparin from solution (Kamil Kamiński, Karolina Zazakowny, Krzysztof Szczubialka, Maria Nowakowska Biomacromolecules 2008, 9(11), 3127-3132.). This polymer is used in form of microspheres or film and it can by potentially used in these forms in the devices for extracorporeal removal of heparin. Polymer in the form of cross-link microspheres or film form cannot be, however, used via intravenously for rapid anti-coagulative effect. For this purpose protamine sulfate is used with all of the negative consequences described above.

Brief Description

Figure 1:
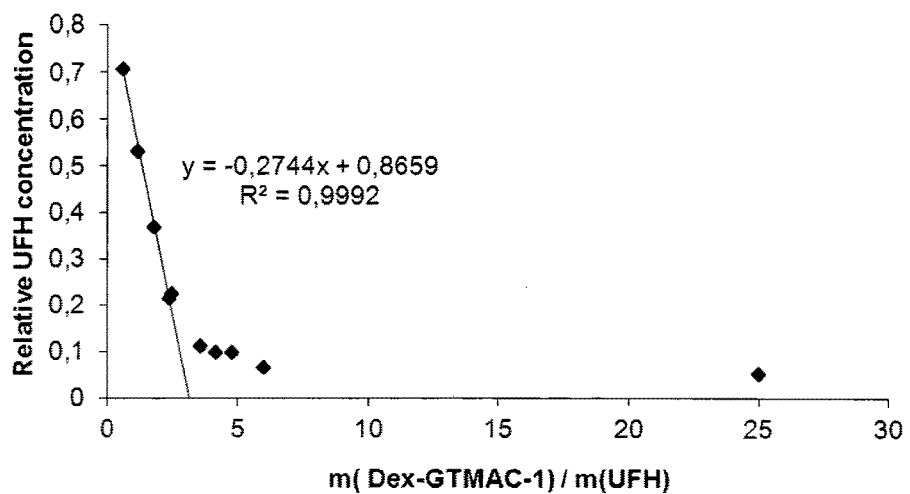
FIG. 1 shows the dependence of UM concentration in the aqueous solution on the mass of added a) Dex-GTMAC-1 and b) Dex-GTMAC-2.
Figure 1:
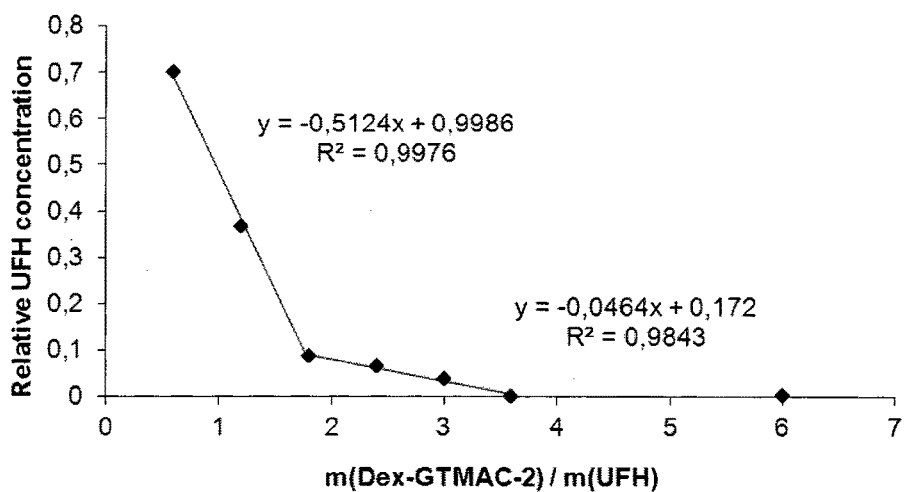

The purpose of the invention was to develop a method of neutralization of anticoagulative action of heparin in blood and body fluids.

The essence of the invention is the use of cationically modified polysaccharides, except for chitosan, to directly neutralize heparin in blood and body fluids of mammals.

The polysaccharides used are preferably modified using compounds containing cationic ammonium group or by grafting with a polymer containing amine or/and ammonium groups. Both methods of modification can be also applied in combination.

Alkyl ammonium halides, chlorides in particular, are preferably used as compounds containing ammonium groups and as monomers to obtain graft polymers.

Glycidyltrimethylammonium chloride or N-acrylamidopropyl-N,N,N-trimethylammonium chloride are preferably used as ammonium chlorides.

Poly(vinyl amine) is preferably used as a polymer containing amine groups.

Dextran or hydroxypropyl cellulose are preferably used as polysaccharides.

Dextran modified with glycidyltrimethylammonium chloride is preferably used.

Hydroxypropyl cellulose grafted with N-acrylamidopropyl-N,N,N-trimethylammonium chloride is preferably used. Hydroxypropyl cellulose grafted with poly(vinyl amine) and possibly modified with glycidyltrimethylammonium chloride is preferably used.

The modified polysaccharide is preferably used as an intravenously administered solution.

The modified polysaccharide is preferably used for heparin neutralization in blood or a in a body fluid obtained from the donor.

Due to the cationic modification the polysaccharides gain the ability to strongly interact with heparin which is polyanion and form a complex with it. Complex formation leads to the loss of its anticoagulative properties. Polysaccharides were selected as complexing polymers due to their beneficial biomedical properties—biocompatibility and nontoxicity. Polysaccharides can be functionalized with small cationic groups or grafted with a polymer containing cationic groups. This way side polymer chains are attached containing many cationic groups. Combination of the above two methods is particularly preferable because low-molecular-weight ammonium compounds used for modification may react easily with amine groups present in the polymer used for grafting of the polysaccharide. For instance grafting poly (vinyl amine) onto hydroxypropyl cellulose allowed for easy cationic modification of the obtained polymer using glycidyltrimethylammonium chloride (GTMAC) because GTMAC reacts easily with amine groups present in poly (vinyl amine).

According to the invention due to the cationic modification polysaccharides became able to form complexes with heparin, and consequently to neutralize its anticoagulative effect.

As polysaccharides dextran and hydroxypropyl cellulose are preferably used, however, other polysaccharides, except for chitosan, can be also used. On the other hand, for modification any low-molecular-weight ammonium compound may be used which contains groups able to react with groups present in a given polysaccharide. For example, in the case of GTMAC the glycidyl group can react with $NH_2$ groups in chitosan or OH groups in dextran, leading to their substitution with GTMAC. In general, compounds which can be used for the cationic modification of a polysaccharide can have very different chemical nature, therefore the polysaccharide modification reactions can be carried out in very different experimental conditions generally known based on the chemical literature.

For grafting of the polysaccharide any ammonium compound can be used which is capable of being polymerized for example by free radical polymerization, controlled radical polymerization, ring opening polymerization, polycondensation or polyaddition. This can be, for example, an ammonium compound containing a vinyl group or hydroxyacid containing an ammonium group. In the case of the free radical polymerization grafting is achieved by formation of free radicals across along the polysaccharide chain (e.g. by the addition of BPO or $KMnO_4$) which initiate side chain growth in the presence of a proper vinyl monomer.

The subject of the invention was presented in more detail in the examples

EXAMPLE 1

Synthesis of Dextran Modified with Glycidyltrimethylammonium Chloride (GTMAC)

2 g of dextran with a molecular mass of 100 000 Da was dissolved in 100 ml of distilled water then the amounts of NaOH and GTMAC were added as given in Table 1. The reaction mixture was heated up to 60° C. The reaction was carried out for 4 hours. The solution containing the reaction product was dialyzed against distilled water until the conductivity decreased down to 2 μS. The polymers obtained were isolated from the solution using the freeze-drying technique. Two polymers were obtained with different degrees of modification and marked as Dex-GTMAC-1 and Dex-GTMAC-2, respectively.

TABLE 1

Weight of the catalyst and GTMAC used during the synthesis of polymers.

| Polymer name | Dex-GTMAC-1 | Dex-GTMAC-2 |
| --- | --- | --- |
| Weight of NaOH catalyst [mg] | 400 | 400 |
| Weight of GTMAC [ml] | 12 | 24 |

For both obtained polymers the degree of modification was determined based on elemental analysis. The results of the elemental analysis of both obtained polymers are shown in Table 2.

TABLE 2

Elemental composition of the modified dextrans.

|  | C % | H % | N % |
|---|---|---|---|
| Dex-GTMAC-1 | 43.605 | 7.223 | 2.02 |
| Dex-GTMAC-2 | 43.61 | 7.29 | 2.86 |

The degree of dextran substitution with GTMAC (defined as a number of molecules of GTMAC attached to a glucose unit), calculated based on the elemental analysis, is 0.48 and 0.67 for Dex-GTMAC-1 and Dex-GTMAC-2, respectively.

Formation of Complexes by Unfractionated Heparin (UFH) and Dex-GTMAC

Relationship between the concentration of free UFH and the concentration of Dex-GTMAC added was investigated using a spectrophotometric method based on Azure A dye. FIG. 1 shows the dependence of UFH concentration in the aqueous solution on the mass of added a) Dex-GTMAC-1 and b) Dex-GTMAC-2. Mass of polymer necessary to bind 90% of 1 mg UFH calculated based on FIG. 1 was 3.15 and 1.95 mg for Dex-GTMAC-1 and Dex-GTMAC-2, respectively.

Formation of Complexes by Low Molecular Weight Heparin (LMWH) and Dex-GTMAC-2

Figure 2:
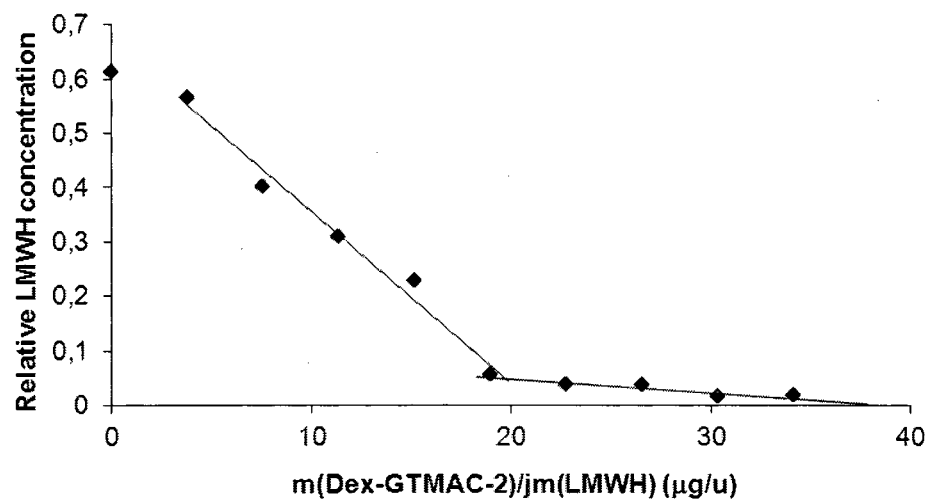
FIG. 2 shows the dependence of the concentration of LMWH in the aqueous solution on the mass of Dex-GTMAC-2.

Analogous studies were carried out on binding of LMWH by Dex-GTMAC-2. It was shown that for binding 90% of LMWH present in the solution requires addition of about 19 µg Dex-GTMAC-2. In FIG. 2 the dependence of the concentration of LMWH in the aqueous solution on the mass of Dex-GTMAC-2 is presented.

EXAMPLE 2

Synthesis of hydroxypropyl cellulose grafted with N-acrylamidopropyl-N,N,N-trimethylammonium chloride 1.5 g of hydroxypropyl cellulose (HPC) was dissolved in 15 mL of DMF. The solution was degassed by bubbling with nitrogen for 30 min. In the same way 7.5 ml of DMF was degassed and 1.35 g of the initiator, benzoyl peroxide (BPO), was added. The two solutions were combined in a three-necked flask which enabled bubbling the reaction mixture with nitrogen during the reaction. After 5 min 17.72 g of 75 wt % N-acrylamidopropyl-N,N,N-trimethylammonium chloride (APTMAC) solution in water was added. The reaction mixture was heated at 70° C. for 3 h under mixing with a magnetic stirrer and constant bubbling with nitrogen. Then the mixture was cooled down, transferred into the dialysis tube and dialyzed for two days first against DMF and after that against a mixture of DMF and water. The fraction of water was gradually increased and finally the dialysis was performed in pure water. The dialysis was carried out against distilled water for two more weeks. The polymer obtained, marked as HPC-APTMAC, was isolated from the solution using freeze-drying technique.

Results of elemental analysis of HPC-APTMAC are shown in Table 3.

TABLE 3

Elemental composition of HPC and HPC-APTMAC

| Polymer | Element content [%] | | | |
|---|---|---|---|---|
|  | C | H | N | C/N |
| HPC | 53.15 | 8.45 | 0 | 0 |
| HPC-APTMAC | 50.33 | 9.078 | 9.29 | 0.18 |

Based on nitrogen content in the polymer the degree of grafting (DG) of HPC by APTMAC was calculated defined as a number of APTMAC molecules attached per 100 glucose units. The calculated average number of APTMAC mers attached do 100 glucose unit is 411.

Formation of Complexes by Heparin and HPC-APTMAC

Figure 3:
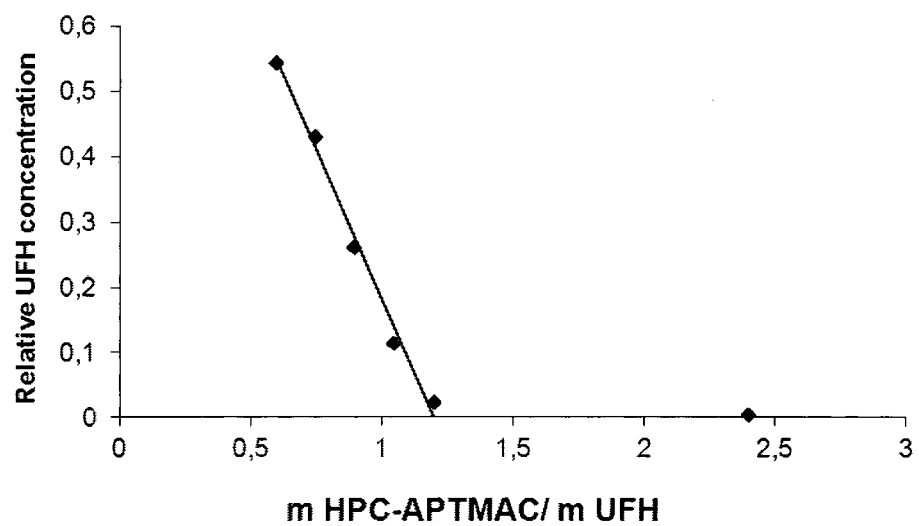
FIG. 3 shows the dependence of the concentration of heparin in the aqueous solution on the mass of added HPC-APTMAC.

Dependence of the concentration of free heparin on the concentration of HPC-APTMAC added was investigated using spectrophotometric method based on the application of Azure A dye. Mass of HPC-APTMAC required to bind 1 mg of heparin, calculated based on the plot, is 1.20 mg. The dependence of the concentration of heparin in the aqueous solution on the mass of added HPC-APTMAC is shown in FIG. 3.

Studies on the Size of HPC-APTMAC Complex with Heparin Using DLS Measurements.

Figure 4:
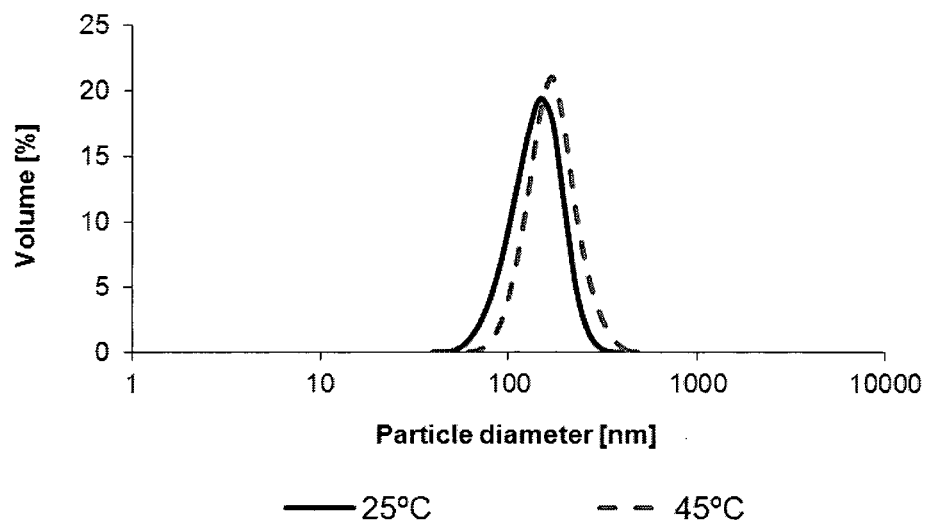
FIG. 4 shows complexes of HPC-APTMAC and heparin are smaller than the complexes of heparin and protamine (148 nm and 1300 nm, respectively) and their size distribution is comparatively narrow.

Using dynamic light scattering technique the size of HPC-APTMAC complexes with heparin obtained by mixing solutions of heparin (0.2 g/l) and HPC-APTMAC (0.6 g/l) was measured. This proportion corresponds to the amount of the polymer sufficient to completely bind heparin as determined using spectrophotometric method. In the FIG. 4. the size distribution of heparin/HPC-APTMAC complexes is shown. It can be seen in FIG. 4 that complexes of HPC-APTMAC and heparin are smaller than the complexes of heparin and protamine (148 nm and 1300 nm, respectively) and their size distribution comparatively narrow. Complexes of such small sizes are easily removed from the bloodstream. In the temperature above LCST the diameter of the complexes is only slightly larger (171 nm) then in the room temperature therefore even at the temperature higher than LCST the complexes are small enough to be easily removed from the body.

EXAMPLE 3

Synthesis of Hydroxypropyl Cellulose Grafted with Poly(Vinyl Amine) and Cationically Modified with Glycidyltrimethylammonium Chloride (GTMAC)

3 g of hydroxypropyl cellulose (HPC) was dissolved in 30 mL of DMF and placed in a closed 250 ml three-necked flask while mixing with a magnetic stirrer. The solution was degassed by bubbling with nitrogen for 30 min. Then 2.7 g (11.16 mM) of benzoyl peroxide BPO dissolved in 15 ml of DMF was added. After 5 min 12.19 g (171.50 mM) of N-vinyl formamide (NVF) was added. The temperature was increased up to 70° C. and the reaction was carried out for 3 hours while continuously mixing and degassing the solution with nitrogen. After 3 hours the reaction mixture was cooled down and dialyzed for one weak first against DMF and then against distilled water. The polymer solution obtained was concentrated using rotary evaporator and the remaining water was removed using freeze-drying technique. After drying 460 mg of obtained polymer was dissolved in 40 ml of distilled water and transferred into a 50 ml round-bottomed flask containing 20 ml of concentrated hydrochloric acid. The reaction mixture was degassed by bubbling with nitrogen for 2 hours. The solution was mixed with the magnetic stirrer for 72 hours and after that it was dialyzed against water until neutral pH was reached. To 50 ml of dialyzed solution (about 50% of the solution obtained during dialysis) 50 mg of NaOH and 5 ml of GTMAC solution was added. The reaction mixture obtained was mixed for 24 hours with a stirrer. After this time the obtained solution was dialyzed against water for 2 weeks.

The composition of HPC used for synthesis was obtained from the elemental analysis (Table 4).

TABLE 4

The elemental composition of HPC used during synthesis

| C % | H % | O % |
|---|---|---|
| 53.147 | 8.455 | 38.398 |

The number of hydroxypropyl groups per one glucose group calculated based on the elemental composition is 3.034.

The elemental composition of HPC grafted with poly(N-vinylformamide) is given in Table 5.

TABLE 5

Elemental composition of HPC grafted with poly(N-vinylformamide)

| C % | H % | N % | O % |
|---|---|---|---|
| 49.989 | 8.279 | 2.039 | 39.692 |

The number of N-vinylformamide units per one glucose group calculated based on the elemental analysis is 0.64.

Based on $^1$H-NMR spectra (relatively small change in the elemental composition does not allow using elemental analysis) it was found that degree of hydrolysis of formamide groups grafted onto a polymer is 50%, therefore the number of $NH_2$ groups per one glucose unit is 0.32. The degree of substitution of $NH_2$ groups with GTMAC molecules, calculated using data from the elemental analysis, is shown in Table 6.

TABLE 6

Elemental composition of HPC grafted with poly(N-vinylformamide) after hydrolysis and modification with GTMAC

| C % | H % | N % |
|---|---|---|
| 48.259 | 8.352 | 2.692 |

Based on the received data degree of substitution of $NH_2$ groups with GTMAC is 0.95. Based on the previous data it was found that the average number of $NH_2$ groups substituted by GTMAC is 30 per 100 glucose units.

Formation of Complexes by Heparin and HPC-PVA-GTMAC a) Unfractionated Heparin

Figure 5:
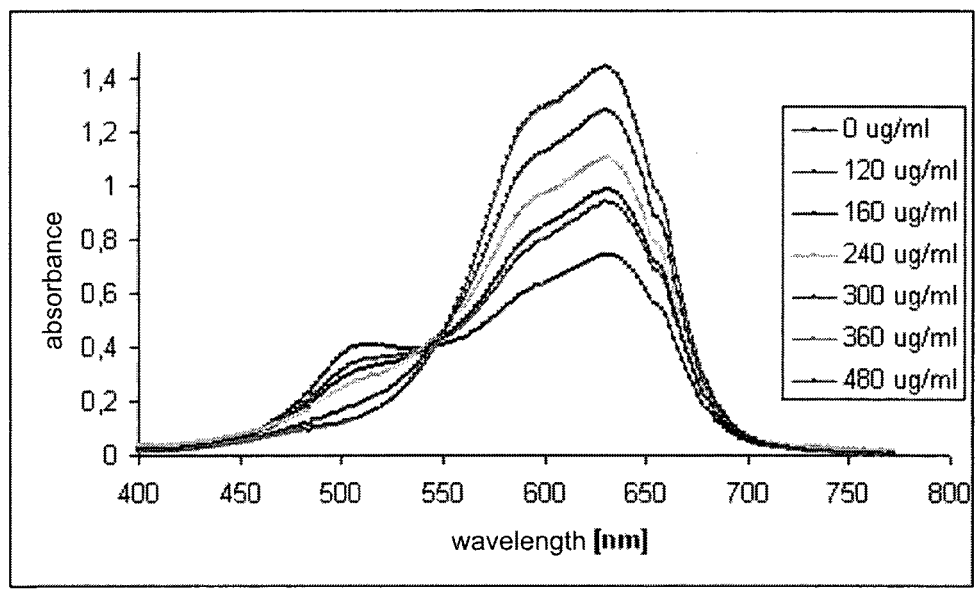
FIG. 5 shows absorption spectra of Azure A solutions ($c=4 \cdot 10^{-5}$ mol/dm$^3$) in pH 7.4 PBS buffer containing UFH (200 μg/ml) in the presence of different HPC-PVA-GTMAC concentrations.
Figure 6:
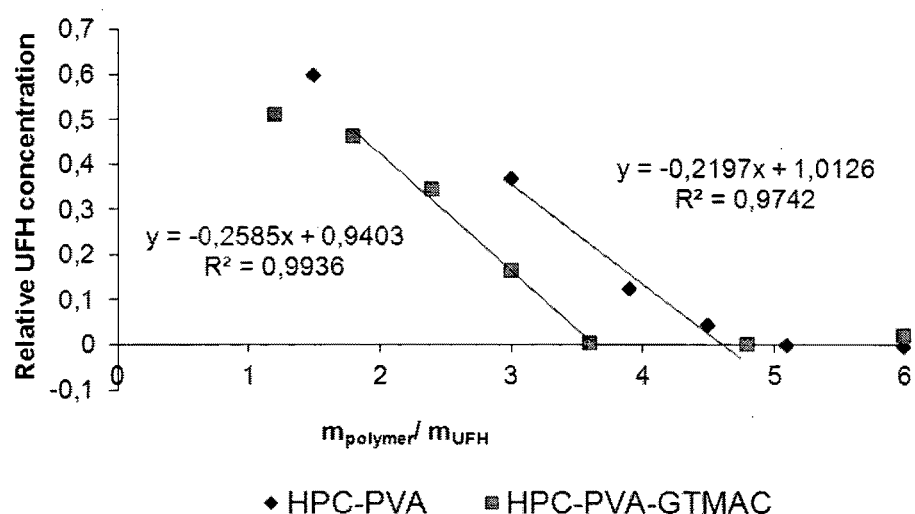
FIG. 6 shows the dependence of heparin concentration in PBS on the mass of added HPC-PVA and HPC-PVA-GTMAC for 1 mg of unfractionated heparin

Studies on the complex formation by HPC-PVA and HPC-PVA-GTMAC with heparin were carried out spectrophotometrically using Azure A as a dye (FIG. 5 absorption spectra of Azure A solutions (c=4·10$^{-5}$ mol/dm$^3$) in pH 7.4 PBS buffer containing UFH (200 µg/ml) in the presence of different HPC-PVA-GTMAC concentrations). It was shown that with increasing concentration of HPC-PVA-GTMAC and HPC-PVA in the solution of unfractionated heparin (UFH) the concentration of free (uncomplexed) heparin decreases. Based on the spectra shown in FIG. 5 the content of free UFH was calculated at a given mass ratio of HPC-PVA and HPC-PVA-GTMAC and UFH (FIG. 6—dependence of heparin concentration in PBS on the mass of added HPC-PVA and HPC-PVA-GTMAC for 1 mg of unfractionated heparin).

Both these polymers form complexes with UFH, the complexation being stronger for HPC-PVA-GTMAC. The quantities of these polymers required to bind 1 mg of UFH are shown in Table 7.

TABLE 7

Mass of polymer required to bind 1 mg of UFH

| Polymer | Mass of polymer required to bind 1 mg of UFH (mg) |
|---|---|
| HPC-PVA | 4.61 |
| HPC-PVA-GTMAC | 3.64 | b) Formation of Complexes of Low Molecular Weight Heparin (LMWH)

Figure 7:
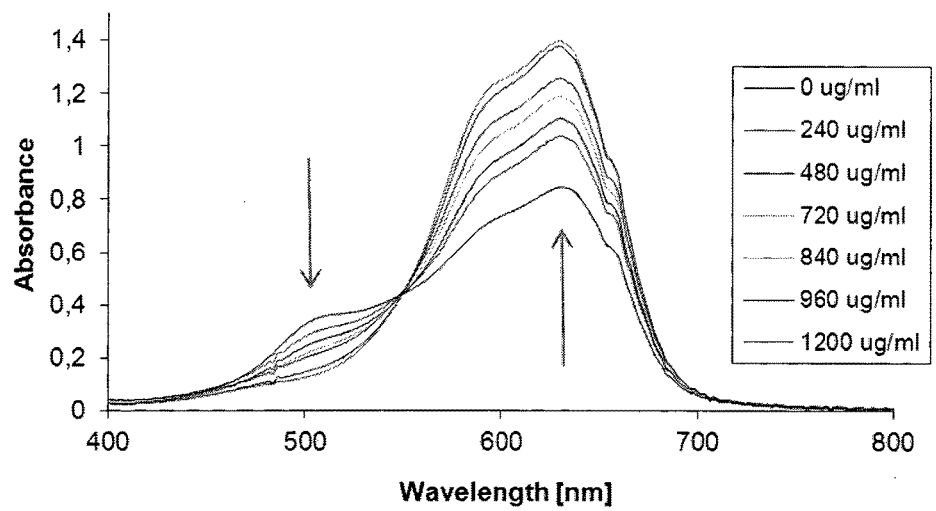
FIG. 7 shows the absorption spectra of Azure A in a pH=7.4 buffer solution containing 28.5 U/ml) in the presence of different concentrations of HPC-PVA-GTMAC.
Figure 8:
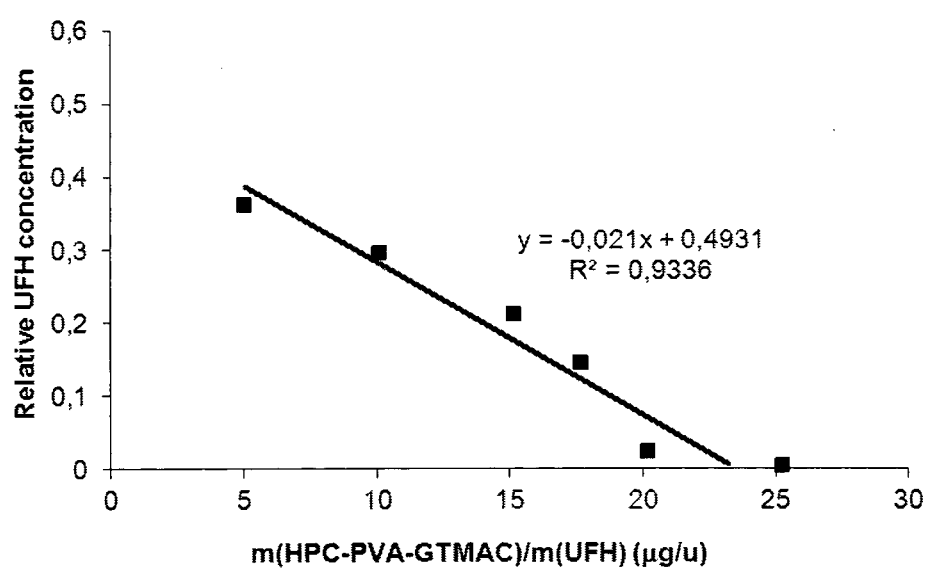
FIG. 8 shows the content of free LMWH as a function of the mass ratio of HPC-PVA-GTMAC and LMWH.

In order to determine mass of HPC-PVA-GTMAC required to complex LMWH the measurements analogous those with UFH were carried out. In FIG. 7 the absorption spectra of Azure A in a pH=7.4 buffer solution containing LMWH (28.5 U/ml) in the presence of different concentrations of HPC-PVA-GTMAC are shown and on FIG. 8 the content of free LMWH as a function of the mass ratio of HPC-PVA-GTMAC and LMWH is presented. The mass of HPC-PVA-GTMAC required to reverse 100 U of LMWH is 2.35 mg.

The invention claimed is:

1. A method of direct neutralization of unfractionated heparin in blood and physiological fluids comprising intravenously administering to a mammal in need thereof cationically modified polysaccharides comprising hydroxypropyl cellulose grafted with N-acrylamidopropyl-N,N,N-trimethylammonium chloride.

2. The method according to claim 1 wherein the hydroxypropyl cellulose grafted with N-acrylamidopropyl-N,N,N-trimethylammonium chloride is used as an intravenous solution.

3. The method according to claim 1 wherein the mammal includes therein blood or physiological fluid obtained from a donor.

4. A method comprising: intravenously administering to a mammal in need of neutralizing anticoagulative effects of unfractionated heparin, a material including an amount of hydroxypropyl cellulose grafted with N-acrlamidopropyl-N,N,N-trimethylammonium chloride sufficient to neutralize such anticoagulative effects, wherein the hydroxypropyl cellulose grafted with N-acrylamidopropyl-N,N,N-trimethylammonium chloride directly neutralizes unfractionated heparin in the blood or physiological fluids in the mammal.

* * * * *